US007796259B2

(12) United States Patent
Tang et al.

(10) Patent No.: US 7,796,259 B2
(45) Date of Patent: Sep. 14, 2010

(54) RAPID ACQUISITION ELLIPSOMETRY

(75) Inventors: Anlun Tang, Pleasanton, CA (US);
Yingwu Lian, Artesia, CA (US); Jonglip Choi, Hayward, CA (US)

(73) Assignee: WeiFour, Inc., Milpitas, CA (US)

( * ) Notice: Subject to any disclaimer, the term of this patent is extended or adjusted under 35 U.S.C. 154(b) by 20 days.

(21) Appl. No.: 12/170,234

(22) Filed: Jul. 9, 2008

(65) Prior Publication Data

US 2010/0007882 A1 Jan. 14, 2010

(51) Int. Cl.
*G01J 4/00* (2006.01)
(52) U.S. Cl. ........................ 356/366; 356/364
(58) Field of Classification Search ............... 356/366, 356/367, 368, 364
See application file for complete search history.

(56) References Cited

U.S. PATENT DOCUMENTS

| | | | | |
|---|---|---|---|---|
| 3,689,163 | A * | 9/1972 | Glorioso | 356/400 |
| 4,198,123 | A * | 4/1980 | Kremen | 359/496 |
| 5,548,404 | A | 8/1996 | Kuperschmidt et al. | |
| 6,181,421 | B1 | 1/2001 | Aspnes et al. | |
| 6,373,569 | B1 * | 4/2002 | Herman et al. | 356/364 |
| 6,850,326 | B2 | 2/2005 | Thoma et al. | |
| 7,061,613 | B1 * | 6/2006 | Huang et al. | 356/364 |
| 7,064,828 | B1 * | 6/2006 | Rovira et al. | 356/369 |
| 2005/0036143 | A1 * | 2/2005 | Huang | 356/369 |

OTHER PUBLICATIONS

An, Ilsin, et al. "Spectroscopic ellipsometry on the millisecond time scale for real-time investigations of thin-film and surface phenomena", *Rev. Sci. Instrum.* (Aug. 1992) 63(8):3842-3848.
Hauge, P.S. "Generalized Rotating-Compensator Ellipsometry", *Surface Science* (1976) 56:148-160.
Hauge, P.S. "Recent Developments in Instrumentation in Ellipsometry", *Surface Science* (1980) 96:108-140.
Lee, Joungchel, et al. "Rotating-compensator multichannel ellipsometry: Applications for real time Stokes vector spectroscopy of thin film growth", *Review of Scientific Instruments* (1998) 69(4):1800-1810.
Hauge, P.S. et al. "A Rotating-Compensator Fourier Ellipsometry", *Optics Communication* (Aug. 1975) 14(4):431-437.
Fujiwari, H. *Spectroscopic Ellipsometry—Principles and Applications* (Mar. 2007) Wiley.

* cited by examiner

*Primary Examiner*—Roy Punnoose
(74) *Attorney, Agent, or Firm*—Townsend and Townsend and Crew LLP

(57) ABSTRACT

Disclosed embodiments pertain to optical assemblies which impart a spatially dependent rotation to linearly polarized light. A pair of optical assemblies may be used to apply a spatially dependent rotation to linearly polarized light in the region between the optical assemblies, and produce a spatially independent rotation after traversing the second optical assembly. A pair of optical assemblies may be used in combination with a wave plate to allow a determination of the Stokes parameters of an elliptically polarized beam of light.

33 Claims, 12 Drawing Sheets

RAPID ACQUISITION ELLIPSOMETRY

BACKGROUND

The application relates generally to surface analysis using electromagnetic radiation (also referred to herein as "light") and particularly to rapid measurements for determining Stokes parameters which describe the polarization of radiation.

Ellipsometry is an extremely sensitive sample analysis technique which can be done non-destructively on most samples. During an ellipsometry experiment, light of one or more wavelengths is reflected from a surface of a sample, or transmitted through the sample and out the other side. Reflected light is more often analyzed and most of the discussion herein pertains to the analysis of reflected light in order to simplify the discussion. The information ellipsometry provides generally characterizes the surface of the sample near the reflection since the reflected light typically interacts less with the sample material away from the surface.

In order to appreciate the principles of ellipsometry, one can visualize the effects a surface may have on a linearly polarized light beam upon reflection. FIG. 1 is a schematic of the optical effects sustained by electromagnetic radiation (also referred to as light) during a reflection from a surface of a sample. FIG. 1 shows a linearly polarized light beam, polarized in a direction 100 composed of a polarization parallel to a plane of incidence 106 (also referred to as p-polarized light) and a polarization perpendicular to the plane of incidence 103 (s-polarized light). The figure shows the oscillations of the electric field at an instant in time. The distance for an oscillation to repeat is the wavelength 107. The light 109 propagates toward the sample 112 and reflects from the surface 113 of the sample 112. The angle of incidence 115 is measured from the surface normal 114 (a line mentally drawn which is perpendicular to the plane of the surface 113).

During the reflection, the light undergoes changes in phases and amplitudes as a result of the interaction with the sample surface. The p-polarized light may sustain a different change-in-phase than the s-polarized light. Similarly, the electric field amplitude of p-polarized (s-polarized) light before reflection may be different from the electric field amplitude of p-polarized (s-polarized) light after reflection. Furthermore, the change in electric field amplitude of p-polarized light before and after reflection may not be the same as the change in electric field amplitude of s-polarized light before and after reflection. Moreover, the ratio of the electric field amplitudes of p-polarized light after and before reflection may not even be the same as the corresponding ratio for s-polarized light. These changes may have different characteristics for a different choice of wavelength 107.

Following a reflection, light propagates away from the sample 118 with the same wavelength but perhaps new amplitudes and phases. The line of propagation after reflection and the line of propagation before reflection occupy a "plane of incidence" as used herein. After reflection, the s-polarized light 124 and the p-polarized light 127 may no longer be coherent. Rather, the oscillations of the s-polarized light 124 and the p-polarized light 127 are separated by a phase angle 130. A non-zero phase angle 130 results in an electric field (interchangeably referred to as the polarization 121) which may not always point in the same direction as the light propagates. The polarization 121 rotates. Once again, the light is depicted at an instant in time to show these details. The polarization 121 also rotates when viewed by a stationary observer. As the light passes a plane 133 the direction of the polarization (the combination of the s-polarized and p-polarized light) rotates counter-clockwise in the schematic illustration. Note that the magnitude is not constant as the elliptical path 134 indicated by arrows is traced.

The polarization of the reflected light is normally determined by characterizing the circumscribed ellipse 134 of FIG. 1. Characterizing the ellipse 134 is one of the steps of ellipsometry and the measurement can be made using a small number of optical elements. Four parameters known as Stokes parameters are often used to describe an optical polarization. The four Stokes parameters ($S_0$, $S_1$, $S_2$ and $S_3$) can be thought of as specifying the size of a Poincaré sphere and a location on the surface of or within the Poincaré sphere. A location within the Poincaré sphere indicates partially polarized light. $S_0$ represents the size of the sphere and the remainder of the parameters represent the location of a point. Roughly speaking, $S_3$ is indicative of how close the ellipse 134 is to a circle and $S_1$, $S_2$ are indicative of the orientation of the ellipse 134 in FIG. 1 as well as whether the polarization 121 rotates clockwise or counter-clockwise.

There are multiple physical arrangements in use for acquiring data which allow the determination of some or all of the Stokes parameters. Measurements which acquire all the Stokes parameters are preferable. Most ellipsometry measurements are made with setups arranged as in FIG. 2. Light 203 originates from a light source 200 and travels toward a polarizer 206 (the polarizer 206 may be represented by the letter "P" herein). Polarized light 207 exits the polarizer 206 and reflects from the surface 212 of a sample 209 (represented by an "S"). The reflected light 213 continues toward a wave plate 221 (represented by a "W"). P-polarized light and s-polarized light travel at different speeds within the wave plate 221 and the thickness is often chosen to impart a quarter wavelength difference in phase between p- and s-polarized light. Such a wave plate 221 is called a quarter wave plate. After emerging from the wave plate 221, the light proceeds toward an analyzer 233 (represented by an "A"). The analyzer may be a polarizer which allows a linearly polarized light beam through to the detector 260. The sequence of objects can be represented succinctly as PSWA.

In these prior art systems, one of the elements may rotate in order to make a measurement of some or all of the Stokes parameters. A subscript "R" may be added to an optical element rotated during a measurement. Table I correlates object sequences with the Stokes parameters which can be determined. The results shown in Table I assume objects without the subscript "R" are stationary during the measurement(s). The position of the sample can be changed from before the wave plate to after the wave plate in $PSWA_R$ and $PSW_RA$ without impacting the list of measurable Stokes parameters.

TABLE I

Physical Arrangement of Prior Art Ellipsometers

| Object Sequence | Measurable Stokes Parameters |
| --- | --- |
| $PSA_R$ | $S_0, S_1, S_2$ |
| $PSWA_R$ | $S_0, S_1, S_2$ |
| $PSW_RA$ | $S_0, S_1, S_2, S_3$ |

The $PSW_RA$ configuration, with a rotating wave plate, enables the determination of four Stokes parameters. Though the four Stokes parameters can be determined, a remaining problem is the speed with which a measurement can be made.

A reliance on rotating or moving optical elements (such as a wave plate) to make a measurement, delays the acquisition of the data needed to determine the Stokes parameters. Besides a reduced throughput, requiring motion of optical requirements introduces significant reliability issues and increases the complexity of data acquisition due, in part, to timing issues.

SUMMARY

Disclosed embodiments pertain to optical assemblies which impart a spatially dependent rotation to linearly polarized light. A pair of optical assemblies may be used to apply a spatially dependent rotation to linearly polarized light in the region between the optical assemblies, and produce a spatially independent rotation after traversing the second optical assembly. A pair of optical assemblies may be used in combination with a wave plate to allow a determination of the Stokes parameters of an elliptically polarized beam of light.

Disclosed embodiments pertain to an optical assembly including an optical element which has an optically-active wedge used to impart a spatially dependent rotation of polarization to linearly polarized light. The optical assembly includes another optical element which has an optically-active wedge to impart a spatially dependent rotation of polarization to linearly polarized light. Together, the two optical elements impart a spatially independent rotation to a linearly polarized light beam.

Further disclosed embodiments pertain to a measurement apparatus for evaluating a sample including a light source, a beam expander to increase the spatial distribution of the light beam, a wave plate assembly, an analyzer, and a one or two-dimensional optical detector. The wave plate assembly includes an optical element which has an optically-active wedge used to impart a spatially dependent rotation of polarization to linearly polarized light. The wave plate assembly includes another optical element which has an optically-active wedge to impart a spatially dependent rotation of polarization to linearly polarized light. Together, the two optical elements impart a spatially independent rotation to a linearly polarized light beam. The wave plate assembly also has a wave plate in between the two optical assemblies during measurements of the sample.

Further disclosed embodiments pertain to a measurement apparatus for evaluating a sample including a light source, a beam expander to increase the spatial distribution of the light beam heading towards the sample, another beam expander to receive light which has reflected from the sample, a wave plate assembly, an analyzer, and a two-dimensional optical detector. The wave plate assembly includes an optical element which has an optically-active wedge used to impart a spatially dependent rotation of polarization to linearly polarized light. The wave plate assembly includes another optical element which has an optically-active wedge to impart a spatially dependent rotation of polarization to linearly polarized light. Together, the two optical elements impart a spatially independent rotation to a linearly polarized light beam. The wave plate assembly also has a wave plate in between the two optical assemblies during measurements of the sample.

Further disclosed embodiments pertain to a measurement apparatus for evaluating a sample including a broad-band light source, a beam expander to receive light which has reflected from the sample, a wave plate assembly, an analyzer, a wavelength-dependent beam expander, and a two-dimensional optical detector. The wave plate assembly includes an optical element which has an optically-active wedge used to impart a spatially dependent rotation of polarization to linearly polarized light. The wave plate assembly includes another optical element which has an optically-active wedge to impart a spatially dependent rotation of polarization to linearly polarized light. Together, the two optical elements impart a spatially independent rotation to a linearly polarized light beam. The wave plate assembly also has a wave plate in between the two optical assemblies during measurements of the sample.

BRIEF DESCRIPTION OF THE DRAWINGS

The present disclosure is described in conjunction with the appended figures.

In the appended figures, similar components and/or features may have the same reference label. Where the reference label is used in the specification, the description is applicable to any one of the similar components having the same reference label.

DETAILED DESCRIPTION

Aspects of embodiments disclosed herein may be used to improve the speed of acquisition of optical metrology systems by enabling optical elements to remain motionless during an acquisition resulting in the determination of the four Stokes parameters. The increase in speed of acquisition enables increases in efficiency when used in production lines and also enable new measurements to be made which took so long previously that the measurements were not practical. Disclosed embodiments remove constraints by using a spatial variation across a wave plate assembly.

Some materials possess the capability of rotating a polarization of light as light traverses (passes through) the material. These are sometimes referred to as optically-active materials. More specifically, materials which rotate the polarization clockwise (as light approaches a viewer) are termed dextrorotary while materials which rotate polarization counter-clockwise are termed levorotary. For a given wavelength, the rotation of the optical polarization is related to the material properties and the thickness of material the light traverses. Optical activity (sometimes called specific rotation or optical rotation) is generally given in units of degrees·$cm^2$/gm.

Figure 1:
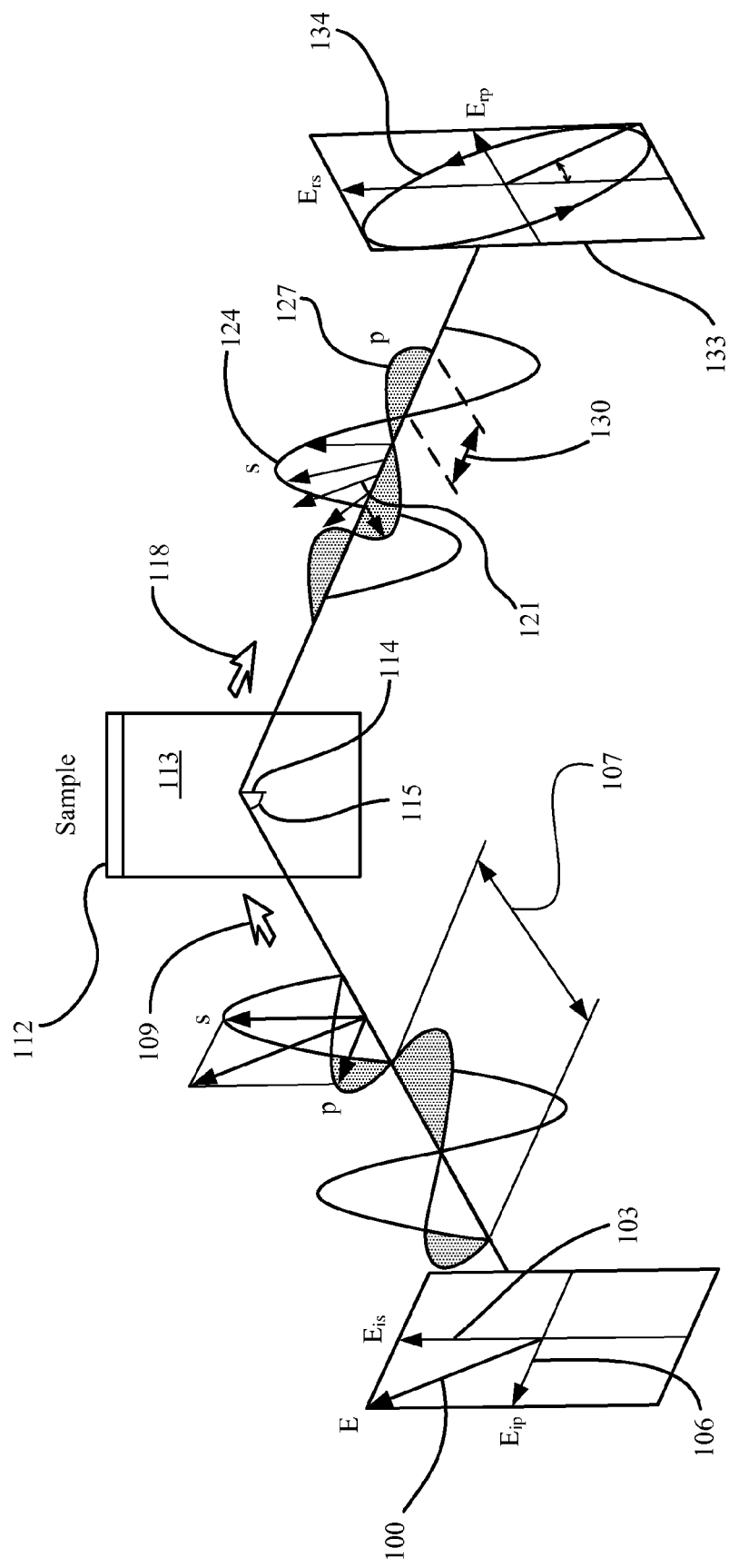
FIG. 1 is a schematic of the optical effects sustained by electromagnetic radiation (also referred to as light) during a reflection from a surface of a sample.
Figure 2:
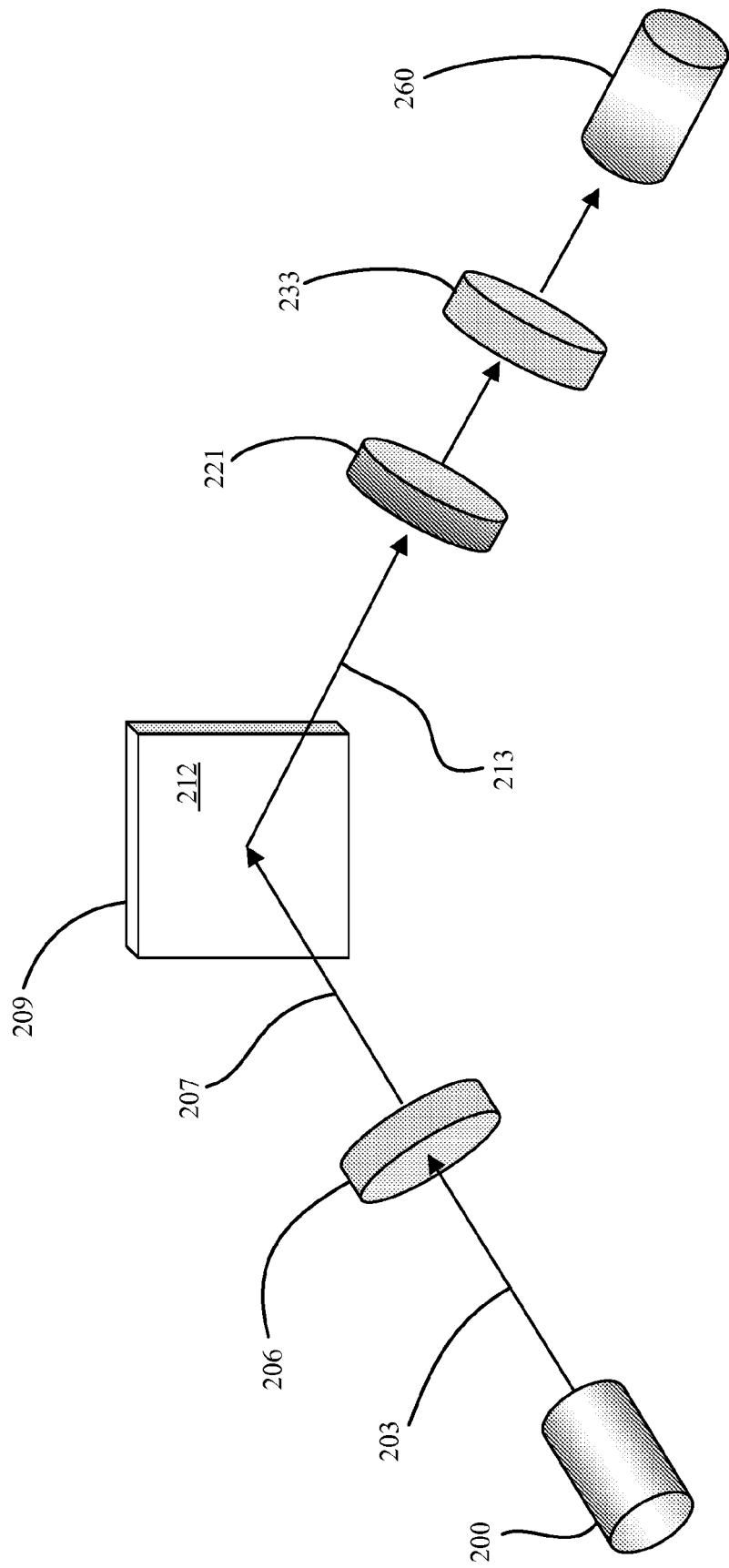
FIG. 2 is a schematic of an ellipsometer.
Figure 3A:
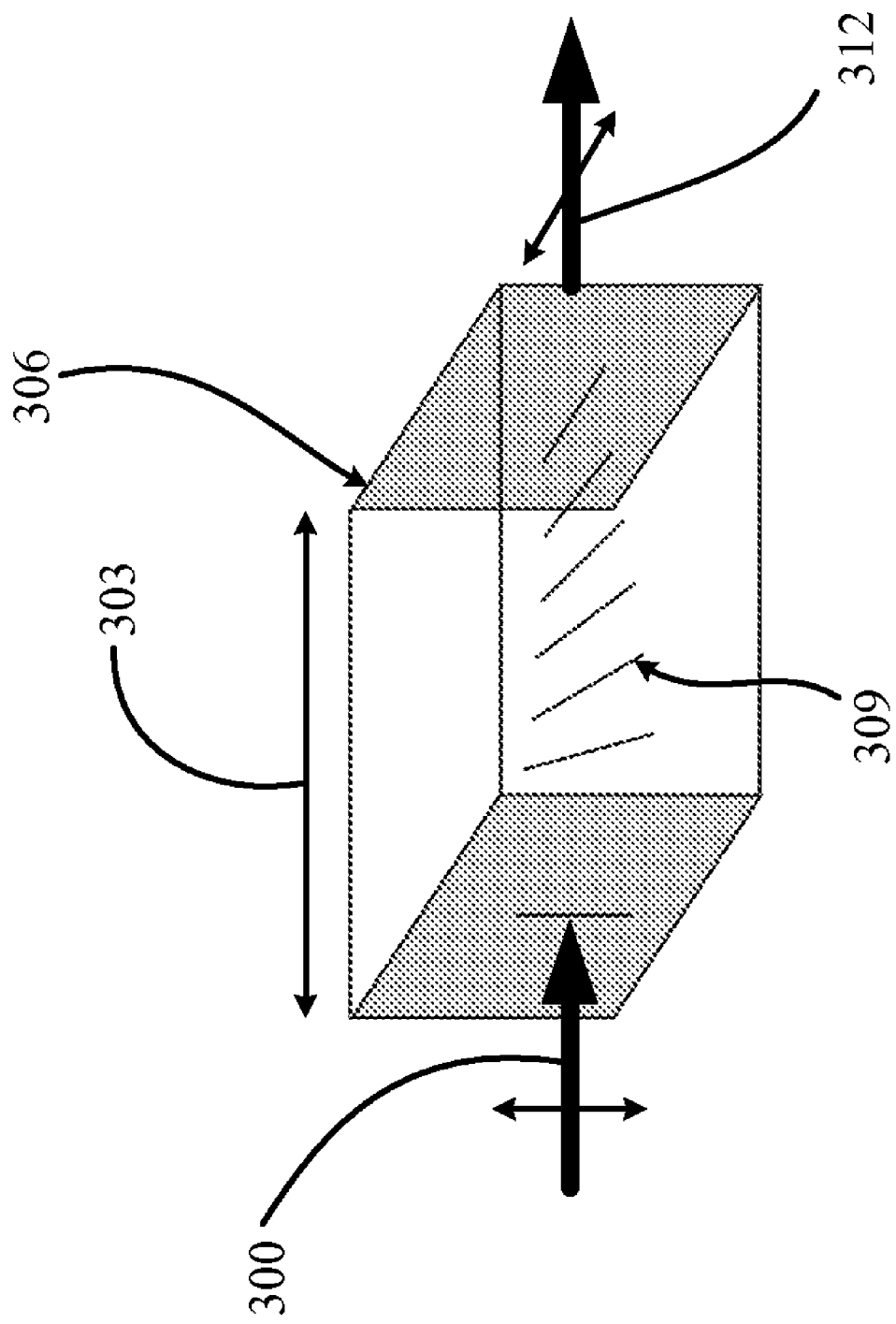
FIG. 3A is a schematic of light traversing optically-active material.

FIG. 3A is a schematic of light traversing a dextrorotary material. A linearly polarized light beam 300 is shown entering the material 306. The polarization of light 309 rotates as the light traverses a thickness 303 of material 306 and emerges as a linearly polarized light beam 312 with polarization rotated 90° clockwise. The thickness of material 306 can be varied to achieve a predetermined rotation of polarization.

There are many examples of dextrorotary (d-rotary) and levorotary (l-rotary) materials with a wide range of optical activities. Optical activities are generally dependent on the wavelength of the passing light. A positive optical activity is used to indicate a dextrorotary material which rotates polarization clockwise (viewed head-on). Other materials used to rotate polarization in the past have optical activities which range from −100 to 300 degrees·cm$^2$/gm when measured at a variety of wavelengths. Many of these materials have an intrinsic optical activity. Intrinsic optical activity may result from a lack of rotational symmetry in a crystalline or molecular structure along the axis of optical propagation. Some materials, e.g. tartaric acid and bromobutane, can be obtained or formed with the same magnitude of optical activity but opposite sign. In other words, tartaric acid and bromobutane may be used to rotate polarization either way depending on the preparation of the material. Materials without an intrinsic optical activity may become optically-active when a magnetic field is applied. In these situations, materials have an extrinsic optical activity.

Figure 3B:
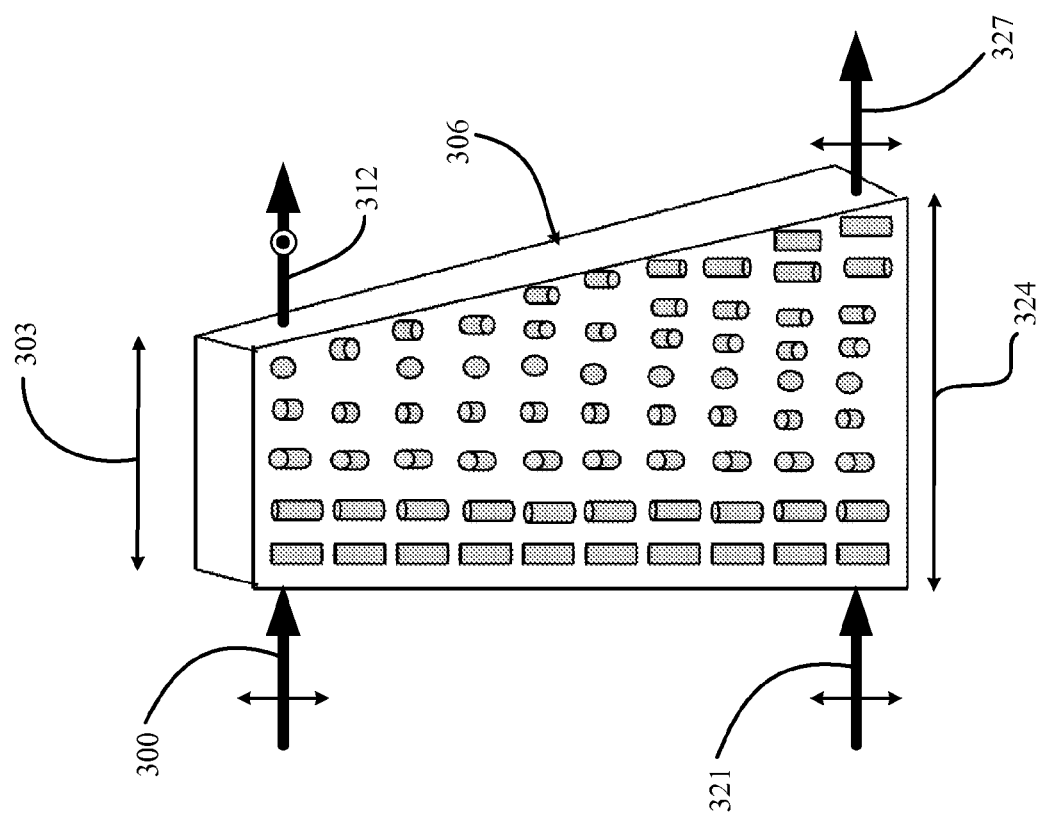
FIG. 3B is a schematic of an optically-active material with spatially varying thickness.

Regardless of the origin of the optical activity, a material can be used to create a spatially varying rotation of polarization by varying the thickness of material through which light traverses. FIG. 3B shows a wedge shape of levorotary material 306. Light is shown entering the wedge at two different locations, each with a vertical linear polarization. A first beam 300 is shown entering from the top left and a second beam is shown entering the wedge 306 from the bottom left 321. The top beam rotates polarization through a shorter thickness 303 of levorotary material than the bottom beam 324. The top beam rotates counter-clockwise 90° and emerges with a horizontal polarization 312. The bottom beam rotates in the same direction but rotates through 180° and emerges with vertical polarization 327. Light beams traversing intermediate thicknesses rotate polarization counter-clockwise by an amount between 90° and 180°. The term "wedge" is used herein to mean any shape of material with a varying thickness along the direction light travels. The thickness does not have to vary at a regular rate nor does the thickness need to vary monotonically across a wedge. A regular and monotonic thickness variation is shown in FIG. 3B.

Figure 4:
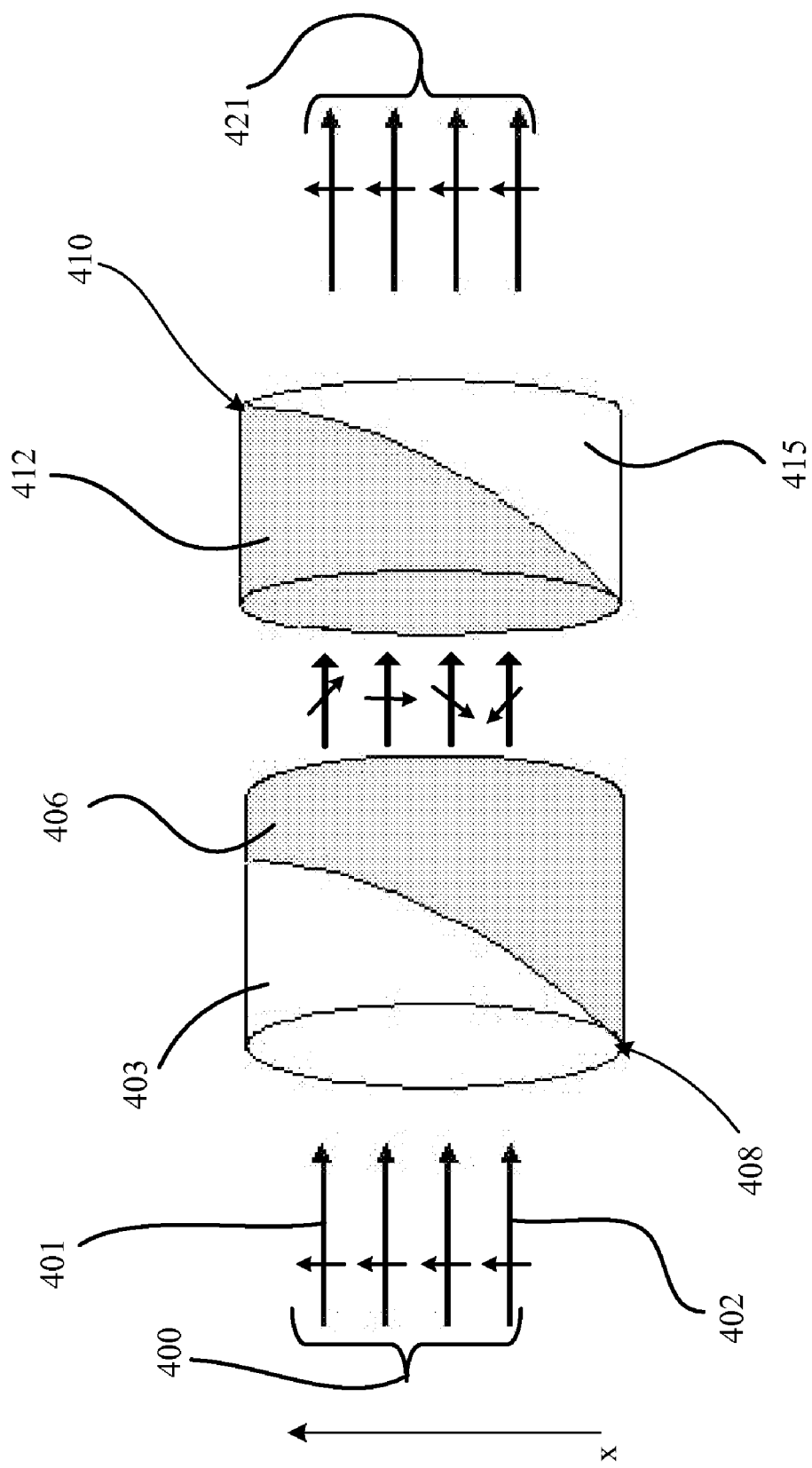
FIG. 4 is a schematic of two optical elements according to disclosed embodiments.

As shown in FIG. 4, a first optically-active wedge 406 can be combined with an index-matched wedge 403 of optically inactive material to create a first optical element 408. The optically inactive material of the index-matched wedge 403 may be selected to possess a similar refractive index to the optically-active material along a path of light near a predetermined wavelength (or range of wavelengths) of light. Light may traverse the first optical element 408 at nearly constant speed regardless of location 400 within the first optical element 408. Using index-matched material also results in less reflection and refraction from the interface within the first optical element 408. For a homogeneous optically-active wedge 406, the wedge can be characterized by a single optical activity and a single refractive index. In such cases, light may traverse a spatially dependent thickness of the optically-active wedge 406 and a spatially dependent thickness of the index-matched wedge 403. However, light may traverse a spatially independent total thickness of material by traversing the combination of the two wedges which form the first optical element 408. The optically-active wedge and the index-matched wedge 403 are homogeneous in some disclosed embodiments. The index-matched wedge 403 may be omitted in some disclosed embodiments.

Light is shown with linear vertical polarization entering the first optical element 408 at spatially varying locations (along the x-axis shown). After light traverses the first optical element 408, light is shown traveling toward a second optical element 410. Within the gap, the light has a variety of polarizations resulting from the spatially dependent thickness of the first optically-active wedge 406. The first optically-active wedge 406 imparts a spatially dependent rotation of polarization to linearly polarized light. The polarization is indicative of the position along the x-axis. The difference in rotation of polarization between the top-most light beam 401 and bottom-most light beam 402 after exiting the first element 400 may be greater than 90°, may be greater than 180° and may be greater than 360° in disclosed embodiments.

The rotated light is shown traveling toward a second optical element 410. The second optical element 410 is configured with an optically-active wedge 412 and an index-matched wedge 415 designed to rotate the polarization of light in the same direction as the first optical element 408. The optically-active wedge 412 is shaped such that, when the second optical element 410 is positioned and oriented properly relative to the first optical element 408, the portions of light emerge from the second optical element 410 with a vertical polarization 421. In this disclosed embodiment the total rotation of the optical polarization is 360° but other angles also work provided that the total rotation angle is a constant, i.e. independent of x. The combination of the first optical element 408 and the second optical element 410, positioned and oriented properly (as shown) relative to the first optical element 408, impart a spatially independent rotation to a linearly polarized light beam traversing the combination of the two optical elements. In the case where the optically-active wedges 406, 412 are homogeneous and have similar optical activities, spatially independent rotation of linearly polarized light occurs when each portion of the light beam traverses nearly the same total thickness of optically active material. A wave plate may be inserted between the two optical elements depicted in FIG. 4, in part, to imitate the effects of rotating a wave plate. Wave plate assemblies involving this configuration are described in detail herein. An analyzer or polarizer, analogously, may be inserted between the two optical elements depicted in FIG. 4 to imitate the effects of rotating an analyzer or polarizer.

Figure 5A:
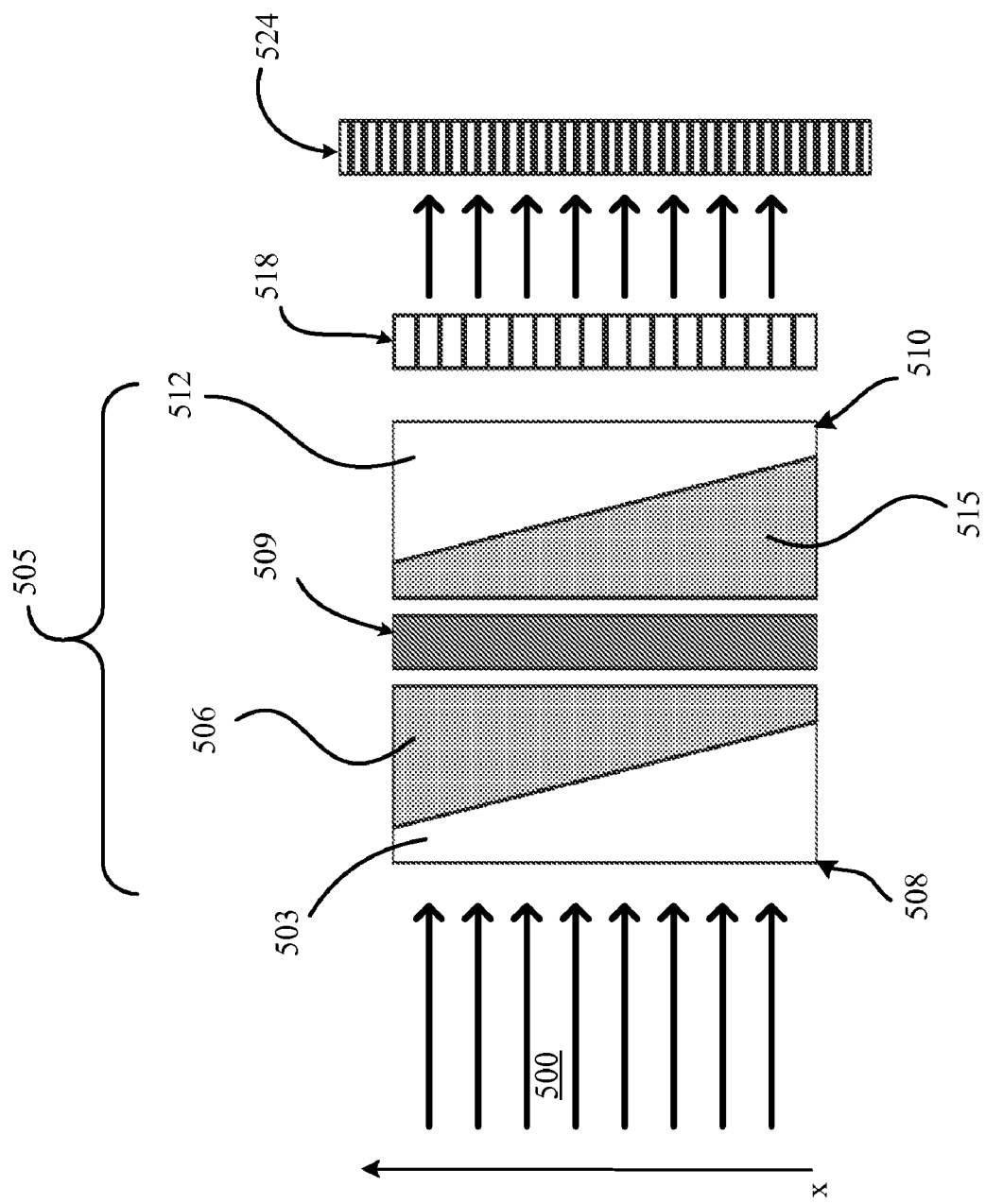
FIG. 5A is a schematic of an optical apparatus incorporating a wave plate assembly according to disclosed embodiments.

In FIG. 5A, two optical elements 508, 510 are shown schematically which can be used in ellipsometry to determine the Stokes parameters. Light 500 reflected from a sample may enter a wave plate assembly 505 made with a first optical element 508. The first optical element 508 rotates the polarization of elliptically polarized light varying amounts depending, in part, upon the path of each particular portion of the light beam. Note that any rotation caused by the first optical element 508 is imparted in combination with any rotation which would normally occur, since the light may be elliptically polarized. The rotated light exits from the first optical element 508, enters the wave plate 509 with varying initial polarizations, traverses the wave plate 509, and traverses the second optical element 510 before continuing on through an analyzer 518 to a detector 524. The detector 524 may be a one or two dimensional array of photo-detector elements used to separately detect light having traversed the wave plate assembly 505 and analyzer 518 along different paths.

The shapes of the interfaces between the optically-active wedges 506, 515 and the index-matched wedges 503, 512 can be non-planar in disclosed embodiments. In non-planar embodiments, the two interfaces may be configured so that the optical rotation of linearly polarized light may still satisfy the following relationship in the absence of the wave plate 509.

$$\theta_1(x)+\theta_2(x)=360°\qquad\text{Eq. 1}$$

where $\theta_1(x)$ and $\theta_2(x)$ are the spatially dependent rotations of polarization experienced as linearly polarized light traverses the first and second optical elements, respectively. In some disclosed embodiments, the sum of the angles, $\theta_1(x)$ and $\theta_2(x)$, is an integer multiple of 360°. In some disclosed embodiments, the sum of the angles, $\theta_1(x)$ and $\theta_2(x)$, is any constant (independent of x).

The optically-active wedge 506 of the first optical element 508 and the optically-active wedge 515 of the second optical element 510 may have different optical activities (or different optical activity distributions when the wedges are inhomogeneous). The sign of the optical activities may be the same but the magnitude of the optical activities may be different. In some disclosed embodiments, the optical activity may vary within an optically-active wedge. In some disclosed embodiments the dimensions of the two optical elements may be adjusted so that the sum of the angles, $\theta_1(x)$ and $\theta_2(x)$, is any constant (independent of x). An optical element made with an optically-active material possessing higher optical activity may be made thinner than an optical element made with an optically-active material possessing lower optical activity.

Figure 5B:
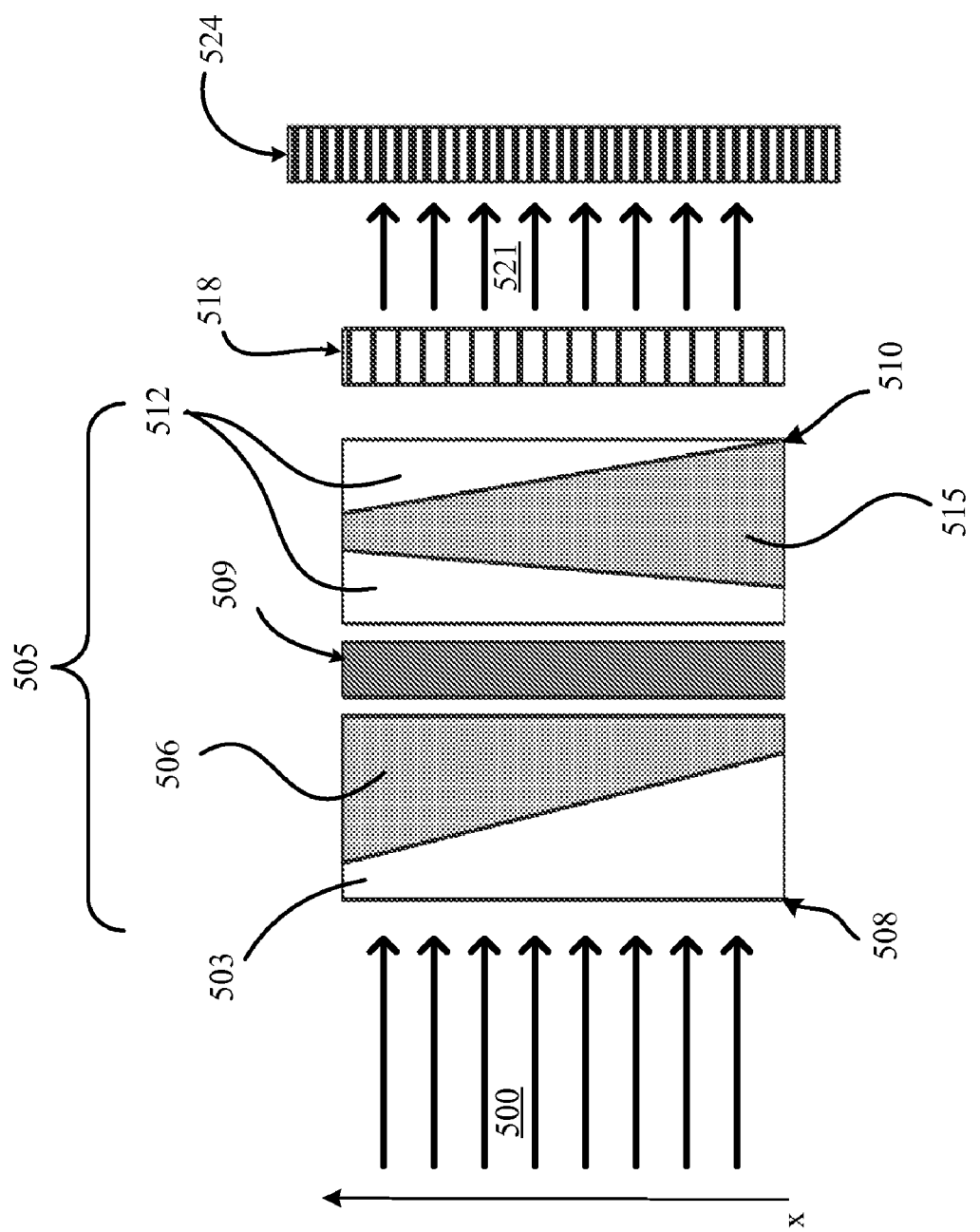
FIG. 5B is a schematic of an optical apparatus incorporating a wave plate assembly according to disclosed embodiments.

FIG. 5B shows a schematic of an optical apparatus with a wave plate assembly 505 present in disclosed embodiments. Light 500 traverses similar proportions of index-matched material 503, 512 and optically-active material 506, 515 to the proportions shown in FIG. 5A. The illustration indicates how two index-matched wedges 512 may be combined with one optically-active wedge to achieve a similar result. Multiple optically-active wedges are also present in a single optical element in disclosed embodiments provided that the angles, $\theta_1(x)$ and $\theta_2(x)$, add up to a 360° or, more generally, any constant (independent of x). An optical detector may benefit from aspects of the disclosed embodiments with a wide variety of optical elements which rotate linearly polarized light as described in the preceding discussion.

Figure 5C:
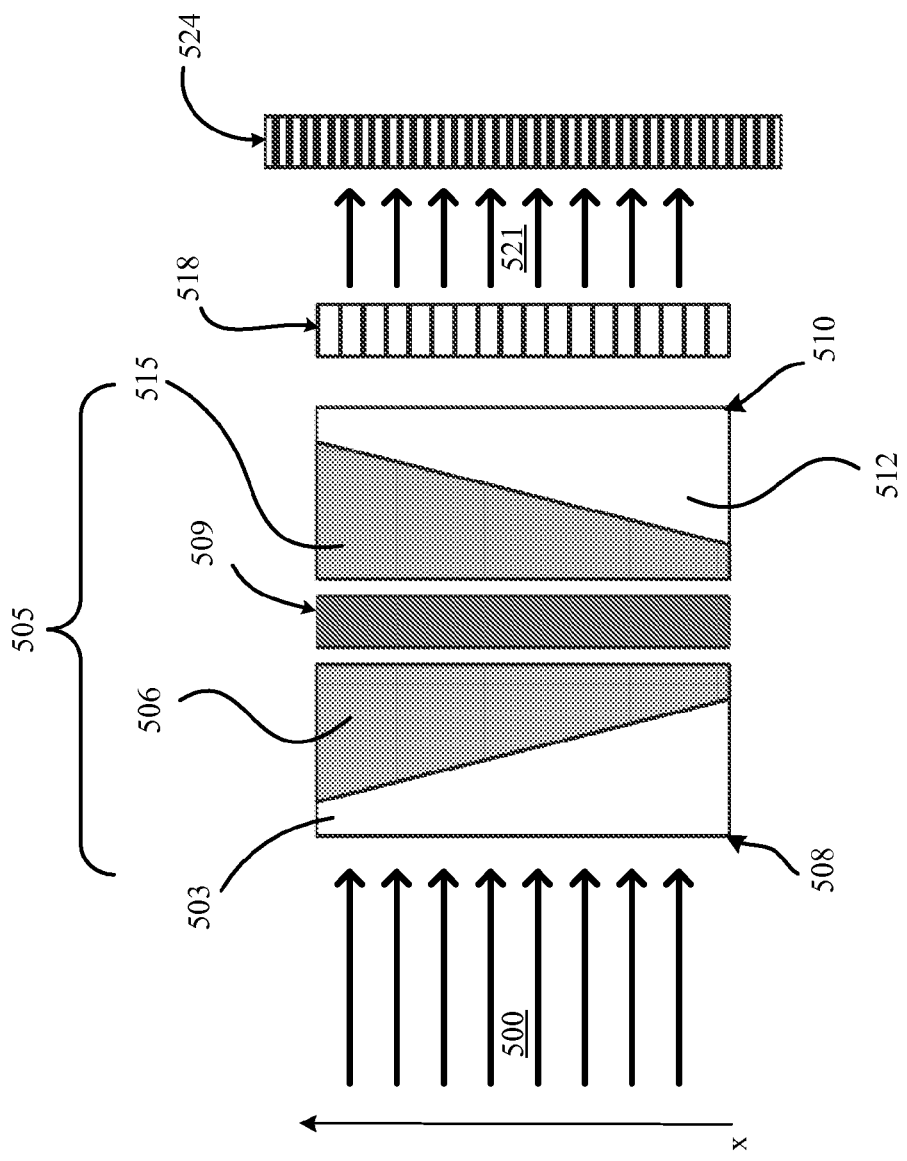
FIG. 5C is a schematic of an optical apparatus incorporating a wave plate assembly according to disclosed embodiments.

The availability of materials which can be made either dextrorotary or levorotary allows the formation of other useful wave plate assemblies. FIG. 5C is a schematic of an optical apparatus incorporating a wave plate assembly 505 according to disclosed embodiments. Light from a sample enters from the left 500 at different physical locations (again represented as x) and traverses an optical element 508 made from an optically-active wedge 506 and an index-matched wedge 503. After traversing a wave plate 509, the light enters an optical element 510 made from an optically-active wedge 515 and an index-matched wedge 512. Here, the optically-active wedge 515 is made from optically-active material which rotates polarization in the opposite direction from the first optically-active wedge 506. Both optically-active wedges have nearly the same magnitude, in some disclosed embodiments, but opposite sign. One of the optically-active wedges is made from dextrorotary material and the other is made from levorotary material. Linearly polarized light traversing both optical elements (with the wave plate removed) would now satisfy Eq. 2.

$$\theta_1(x)+\theta_2(x)=0°\qquad\text{Eq. 2}$$

A rotation imparted by the first optical element 508 on linearly polarized light is substantially reversed by the rotation imparted by the second optical element 510. This reversal occurs regardless of where along the x-axis the light enters the first optical element 508.

The optically-active wedge 506 of the first optical element 508 and the optically-active wedge 515 of the second element 510 may be made from optically-active materials with differing magnitudes of optical activity. The sign of the optical activities may be opposite (one levorotary and one dextrorotary) and the magnitudes of the optical activities may be different. In some disclosed embodiments, the magnitude of the optical activity may vary within an optically-active wedge. The dimensions of the two optical elements may be adjusted so that the sum of the angles, $\theta_1(x)$ and $\theta_2(x)$, is any constant (independent of x). An optical element made with an optically-active material possessing a higher magnitude of optical activity may be made thinner than an optical element made with an optically-active material possessing a lower magnitude of optical activity.

Figure 6:
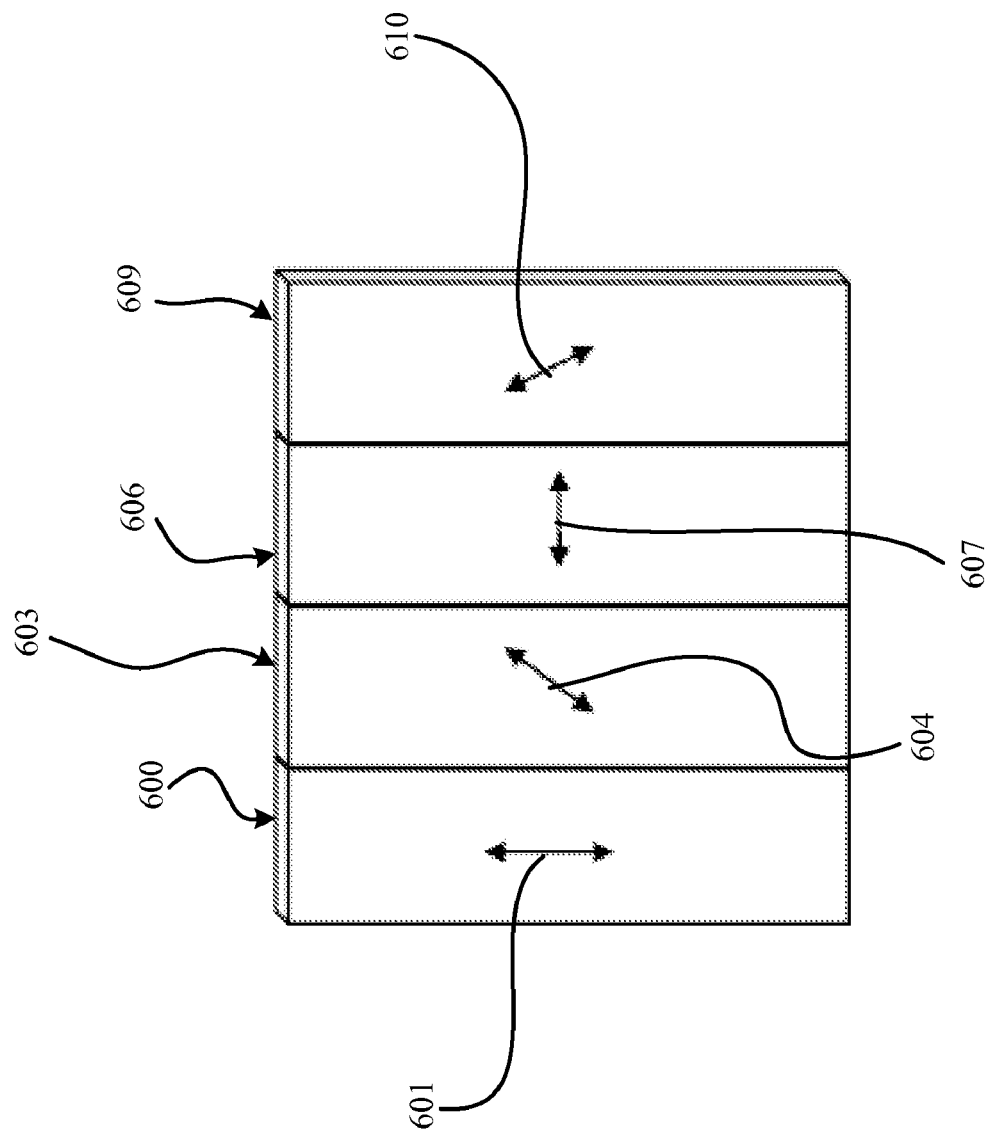
FIG. 6 is a schematic of a wave plate assembly according to disclosed embodiments.

FIG. 6 shows another method of creating a wave plate assembly. This type of wave plate assembly also allows the wave plate assembly to remain stationary during a measurement acquisition while still acquiring data for different wave plate orientations. Discrete slabs (600, 603, 606 & 609) of wave plates are shown in FIG. 6 with "fast" axes pointing in different directions (601, 604, 607 & 610). Light polarized in the "fast" direction will travel at a higher speed than light polarized in a "slow" direction. The discrete slabs shown have "fast" axes oriented every 45°. A wave plate, assembled in this way, may be substituted for a rotating wave plate in a measurement apparatus. A similar discrete design may be made with optically active slabs. Discrete slabs of different optically-active materials and/or different thicknesses of optically-active materials may also be combined to form a simpler optically-active wedge. Wedges such as these may be used as alternatives to the more continuously varying wedges described herein. In some disclosed embodiments, the data acquired at the detector is analogous to taking data with a rotating wave plate and acquiring data every time the wave plate rotates through 45°. Analysis is performed by using a one or two dimensional array of photo-detecting elements and, in embodiments, averaging the array elements which detect light having traversed the same slab. The sampling is less complete than when more continuously varying optically-active wedges or wave plates are used. However, for simple samples which may involve material models with few degrees of freedom, this may prove useful. A larger number of smaller, but still discrete, slabs can be used to improve the resolution.

Figure 7A:
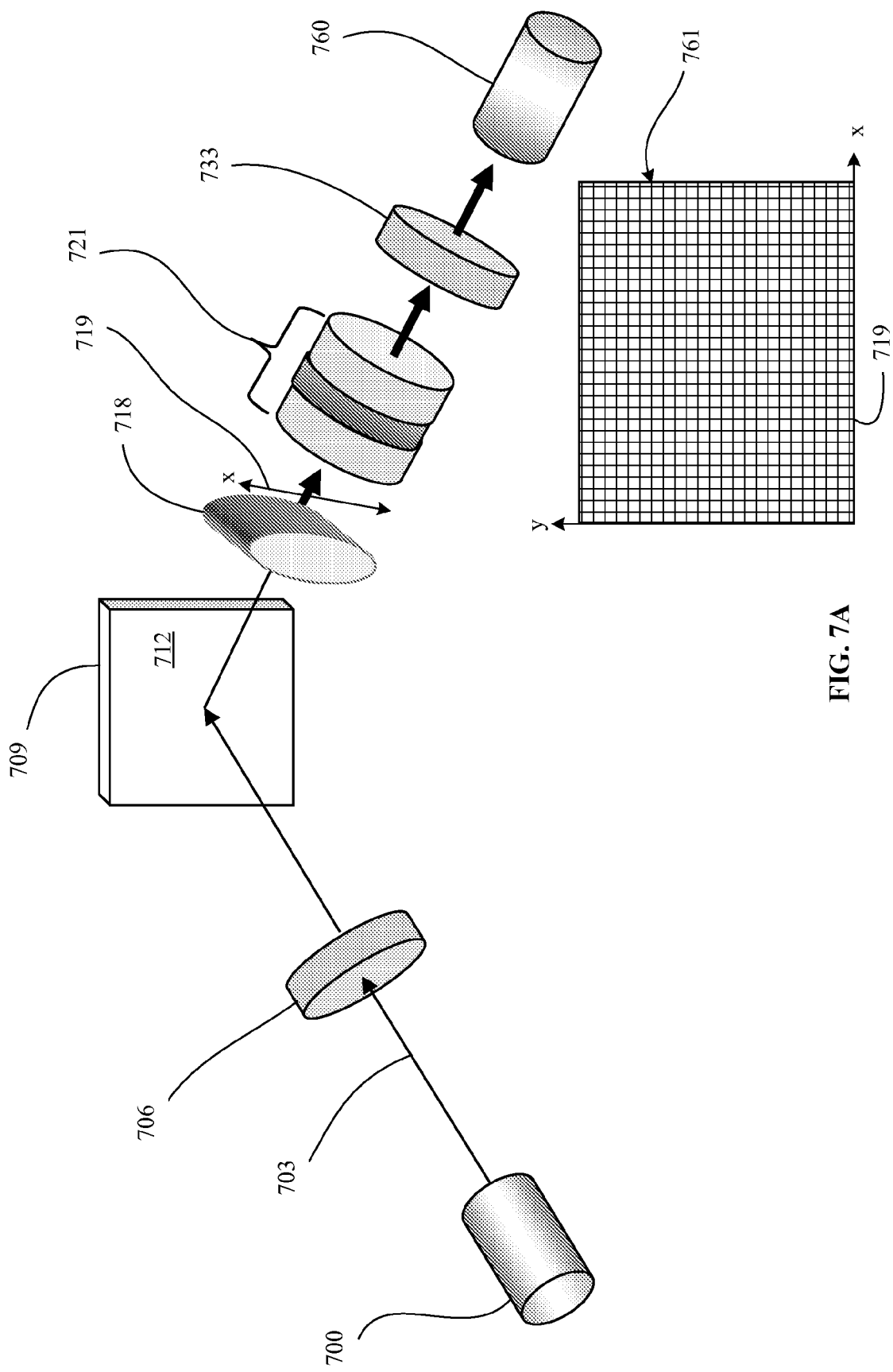
FIG. 7A is a schematic of an ellipsometer according to disclosed embodiments.
Figure 7B:
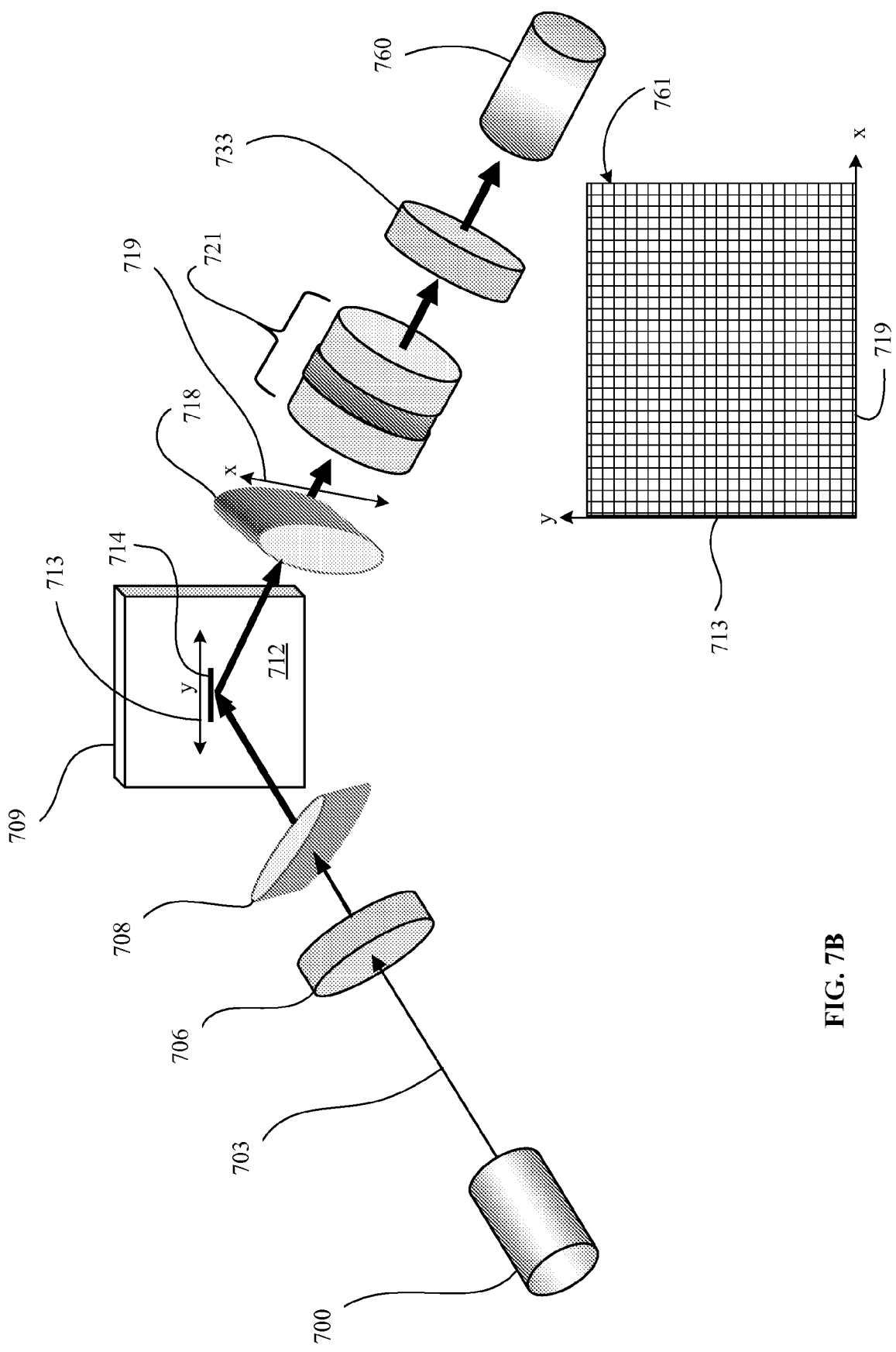
FIG. 7B is a schematic of an ellipsometer according to disclosed embodiments.
Figure 7C:
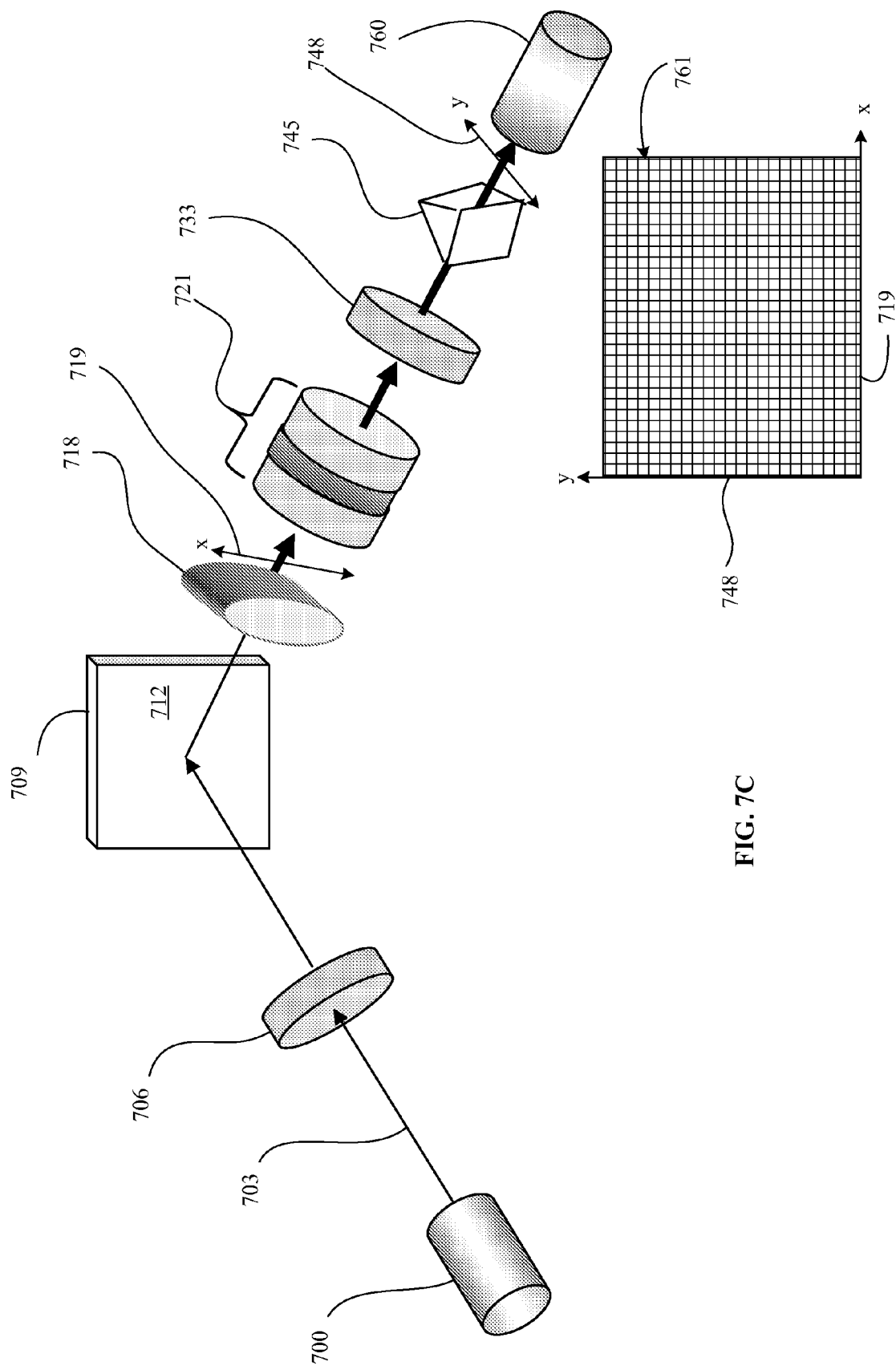
FIG. 7C is a schematic of an ellipsometer according to disclosed embodiments.

The wave plate assemblies described herein are shown in various ellipsometry applications in FIGS. 7A-C. In FIG. 7A, light originates from a light source 700 and traverses a polarizer 706, reflects from a surface 712 of a sample 709 and is expanded along one dimension 719 by a beam expander 718 before traversing a wave plate assembly 721. The light then traverses an analyzer and is detected by a detector 760 with a two dimensional array 761 of photo-detector elements. One axis 719 of the detector represents the location light traverses the wave plate assembly. An array of optical intensities is analyzed in a manner similar to data acquired from a rotating wave plate apparatus. Data can be averaged along a perpendicular axis to the spatially dependent axis 719 of the detector to improve signal-to-noise ratio.

In order to process data from the detector in an analogous way to a prior art rotating-wave plate apparatus, a correlation may be made between position along the x-axis of the detector and the rotation imparted by one of the optical elements on linearly polarized light. The imparted rotation may be calculated, for homogeneous optically active materials, from the product of the optical activity and the thickness of the optically-active wedge (which depends on x). The imparted rotation also may be measured by passing linearly polarized light through one of the optical elements, then the analyzer and then into the photo-detector array. A sinusoidal waveform may be present on the detector which allows the determination of the number of pixels needed to represent 90°, 180° or 360° of rotation as desired in disclosed embodiments.

A third way to calibrate the array of photo-detector is to simply fit the function governing the optical intensity expected for different wave plate angles. The functional form is shown in Eq. 3.

$$I=I_0\{2+S_1-2S_3 \sin 2W+S_1 \cos 4W+S_2 \sin 4W\} \quad \text{Eq. 3}$$

where W is the angle of the wave plate in a rotating wave plate apparatus. In the embodiments disclosed herein, W is the angle linearly polarized light is turned before entering the wave plate. In other words, W is a function of x. With the disclosed embodiment of FIG. 7A, the function of Eq. 3 can be fit to the optical intensity detected along the x-axis substituting ax+b for W in the equation. The data can then be fit to determine the six parameters: a, b, $S_1$, $S_2$, $S_3$ and $I_0$. The first two methods of calibrating the detector provide a way to determine a and b and therefore simplify the fitting procedure. A simpler fitting procedure results in a more accurate determination of the Stokes parameters.

Wave plate assemblies present in disclosed embodiments enable the Stokes parameters to be determined with a simultaneous acquisition instead of acquiring a time-sequence of measurements with a rotating wave plate. The time of acquisition can be reduced from several milliseconds or more to several microseconds which makes new applications possible. FIG. 7B is a schematic of an ellipsometer which may be used to make simultaneous measurements at more than one location on the surface of a sample. Such an ellipsometer may be used in an application involving simultaneous determination of the Stokes parameters along a line 713 of an illuminated portion 714 of the sample 709. The beam of light is expanded by a beam expander 708 to illuminate an elongated portion 714 of the sample 709. The axes of the two dimensional array of photo-detectors can be indicative of the position along the illuminated region 714 and the location, x, light enters the wave plate assembly 719.

Spectroscopic ellipsometry (SE) is a technique used in the prior art to analyze a distribution of wavelengths simultaneously with an array of photo-detector elements and an optical element placed after the analyzer to separate the distribution of wavelengths spatially. Such an optical element may be a prism 745 but may be other elements known to those of ordinary skill in the art. Wave plate assemblies, according to disclosed embodiments, can be used to determine the Stokes parameters at a distribution of wavelengths without rotating or modulating optical elements. A schematic of an embodiment combining spectroscopic ellipsometry with a wave plate assembly is shown in FIG. 7C. A prism 745 may be used to spatially separate different wavelengths of light which are detected along the y-axis 748 of the photo-detector array. The x-axis 719, again, may represent the location illumination traverses the wave plate assembly 721. Since optical activity is generally a function of wavelength, each wavelength may be calibrated separately in disclosed embodiments.

Herein, use of the terms similar to "light", "optical" and "optics" does not carry any implication that the electromagnetic radiation involved is within the visible portion of the spectrum. The light can be of any wavelength. Use of the term "stationary" means that the elements so described are stationary in the frame of reference of the detector, light source, and sample.

It will also be recognized by those skilled in the art that, while the invention has been described above in terms of preferred embodiments, it is not limited thereto. Various features and aspects of the above-described invention may be used individually or jointly. Further, although the invention has been described in the context of its implementation in a particular environment and for particular applications, those skilled in the art will recognize that its usefulness is not limited thereto and that the present invention can be utilized in any number of environments and implementations.

What is claimed is:

1. An optical assembly comprising:
    a first optical element comprising a first optically-active wedge configured to impart a first spatially dependent rotation of polarization to linearly polarized light traversing in a first direction, wherein the first optical element further comprises a first index-matched wedge configured such that a light beam traveling in the first direction traverses a spatially independent thickness of the first optical element; and
    a second optical element comprising a second optically-active wedge configured to impart a second spatially dependent rotation of polarization to linearly polarized light traversing in a second direction;
    wherein there exists an orientation of the second optical element relative to the first optical element such that a linearly polarized light beam traversing the first optical element in the first direction and traversing the second optical element in the second direction results in a spatially independent rotation of the polarization.

2. The optical assembly of claim 1 wherein the second optical element further comprises a second index-matched wedge configured such that a light beam traveling in the second direction traverses a spatially independent thickness of the second optical element.

3. The optical assembly of claim 1 further comprising a wave plate disposed between the first optical element and the second optical element.

4. The optical assembly of claim 3 wherein the wave plate is a quarter wave plate.

5. The optical assembly of claim 1 wherein the first optically-active wedge comprises two substantially flat surfaces such that a thickness of the first optically-active wedge varies at a regular rate in at least one dimension.

6. The optical assembly of claim 1 wherein:
    the first optically-active wedge is homogeneous and is characterized by a first optical activity;
    the second optically-active wedge is homogeneous and is characterized by a second optical activity, wherein the second optical activity has a same sign as the first optical activity and a similar magnitude to the first optical activity; and
    the optical assembly is configured such that even though a thickness of the first optically-active wedge and a thickness of the second optically-active wedge vary spatially, each portion of a light beam traverses nearly the same total thickness of optically-active material.

7. The optical assembly of claim 1 wherein:
    the first optically-active wedge is homogeneous and is characterized by a first optical activity;
    the second optically-active wedge is homogeneous and is characterized by a second optical activity, wherein the second optical activity has an opposite sign to the first optical activity and a similar magnitude to the first optical activity; and the optical assembly is configured such that even though a thickness of the first optically-active wedge and a thickness of the second optically-active wedge vary spatially, a portion of a light beam which traverses a first thickness of the first optically-active wedge also traverses a similar thickness of the second optically-active wedge.

8. A measurement apparatus for evaluating a sample comprising:

a light source for generating a light beam, wherein the light beam is substantially collimated;

a beam expander configured to receive the light beam after interaction with the sample and configured to increase a spatial distribution of the light beam along an expansion axis;

a wave plate assembly comprising:

a first optical element comprising a first optically-active wedge configured to impart a first spatially dependent rotation of polarization to linearly polarized light traversing in a first direction, wherein the first optical element further comprises a first index-matched wedge configured such that a light beam traversing in the first direction traverses a spatially independent thickness of the first optical element;

an analyzer; and an optical detector comprising an array of photo-detector elements in at least one dimension.

9. The measurement apparatus of claim 8 wherein the array of photo-detector elements in at least one dimension, comprises an array of photo-detector elements with at least one dimension substantially aligned with the expansion axis.

10. The measurement apparatus of claim 8 wherein the light source comprises a laser.

11. The measurement apparatus of claim 8 wherein the wave plate assembly further comprises a wave plate disposed in the path of the light beam.

12. The measurement apparatus of claim 11 wherein the wave plate assembly further comprises a second optical element comprising a second optically-active wedge configured to impart a second spatially dependent rotation of polarization to linearly polarized light traversing in a second direction, wherein the first optical element and the second optical element are configured to impart a spatially independent rotation to a linearly polarized light beam traversing the first optical element in the first direction and traversing the second optical element in the second direction in the absence of the wave plate, and wherein the wave plate is disposed between the first optical element and the second optical element.

13. The measurement apparatus of claim 12 wherein the second optical element further comprises a second index-matched wedge configured such that a light beam traveling in the second direction traverses a spatially independent thickness of the second optical element.

14. The measurement apparatus of claim 12 wherein the first optical element, the second optical element and the wave plate are configured to remain motionless relative to each other during a measurement which results in indicators of four Stokes parameters.

15. The measurement apparatus of claim 12 wherein the wave plate assembly and the sample are configured to remain motionless relative to each other during a measurement which results in indicators of four Stokes parameters.

16. The measurement apparatus of claim 12 wherein:
the first optically-active wedge is homogeneous and is characterized by a first optical activity;

the second optically-active wedge is homogeneous and is characterized by a second optical activity, wherein the second optical activity has a same sign as the first optical activity and a similar magnitude to the first optical activity; and the wave plate assembly is configured such that even though a thickness of the first optically-active wedge and a thickness of the second optically-active wedge vary spatially, each portion of the light beam traverse nearly the same total thickness of optically-active material.

17. The measurement apparatus of claim 12 wherein:
the first optically-active wedge is homogeneous and is characterized by a first optical activity;

the second optically-active wedge is homogeneous and is characterized by a second optical activity with the opposite sign as the first optical activity and having a similar magnitude to the first optical activity; and the wave plate assembly is configured such that even though a thickness of the first optically-active wedge and a thickness of the second optically-active wedge vary spatially, a portion of the light beam which traverses a first thickness of the first optically-active wedge traverses a second thickness of the second optically-active wedge, wherein the first thickness and the second thickness are nearly the same.

18. The measurement apparatus of claim 11 wherein the wave plate comprises a quarter wave plate.

19. A measurement apparatus for evaluating a sample comprising:

a light source for generating a substantially collimated light beam;

a first beam expander configured to increase the spatial distribution of the substantially collimated light beam along a first expansion axis to elongate the irradiated portion of the sample;

a second beam expander configured to receive light which has reflected from the sample and configured to increase the spatial distribution of the light beam along a second expansion axis;

a wave plate assembly, the wave plate assembly comprising:

a first optical element comprising a first optically-active wedge and a first index-matched wedge, wherein a thickness of the first optically-active wedge parallel to a path of the light beam varies spatially and the thickness of the first optically-active wedge in combination with the first index-matched wedge is spatially constant parallel to the path of the light beam;

an analyzer; and an optical detector comprising a two dimensional array of photo-detector elements.

20. The measurement apparatus of claim 19 wherein the first expansion axis and the second expansion axis are substantially orthogonal.

21. The measurement apparatus of claim 19 wherein at least one dimension of the two dimensional array is substantially aligned with the first expansion axis.

22. The measurement apparatus of claim 19 wherein at least one dimension of the two dimensional array is substantially aligned with the second expansion axis.

23. The measurement apparatus of claim 19 wherein the wave plate assembly further comprises a wave plate disposed in the path of the light beam.

24. The measurement apparatus of claim 23 wherein the wave plate comprises a quarter wave plate.

25. The measurement apparatus of claim 23 wherein the wave plate assembly further comprises a second optical element comprising a second optically-active wedge and a second index-matched wedge, wherein a thickness of the second optically-active wedge parallel to the path of the light beam varies spatially whereas the thickness of the second optically-active wedge in combination with the second index-matched wedge is spatially constant parallel to the path of the light beam, wherein the wave plate is disposed between the first optical element and the second optical element.

26. A spectroscopic measurement apparatus for evaluating a sample comprising:
- a broad-band light source for generating a substantially collimated light beam with at least two wavelengths;
- a beam expander configured to receive light which has reflected from the sample and configured to increase the spatial distribution of the light beam along a first expansion axis;
- a wave plate assembly, the wave plate assembly comprising:
  - a first optical element comprising a first optically-active wedge and a first index-matched wedge, wherein a thickness of the first optically-active wedge parallel to a path of the light beam varies spatially and the thickness of the first optically-active wedge in combination with the first index-matched wedge is spatially constant parallel to the path of the light beam;
- an analyzer;
- a wavelength-dependent beam expander configured to increase the spatial distribution of the substantially collimated light beam along a second expansion axis so a location along the expansion axis is indicative of an optical wavelength; and
- an optical detector comprising a two dimensional array of photo-detector elements, wherein a first dimension is aligned with the first expansion axis and a second dimension is aligned with the second expansion axis.

27. The measurement apparatus of claim 26 wherein the first expansion axis and the second expansion axis are substantially orthogonal.

28. The measurement apparatus of claim 26 wherein at least one dimension of the two dimensional array is substantially aligned with the first expansion axis.

29. The measurement apparatus of claim 26 wherein at least one dimension of the two dimensional array is substantially aligned with the second expansion axis.

30. The measurement apparatus of claim 26 wherein the wavelength-dependent beam expander comprises a prism.

31. The measurement apparatus of claim 26 wherein the wave plate assembly further comprises a wave plate disposed in the path of the light beam.

32. The measurement apparatus of claim 31 wherein the wave plate comprises a quarter wave plate.

33. The measurement apparatus of claim 31 wherein the wave plate assembly further comprises a second optical element comprising a second optically-active wedge and a second index-matched wedge, wherein a thickness of the second optically-active wedge parallel to the path of the light beam varies spatially whereas the thickness of the second optically-active wedge in combination with the second index-matched wedge is spatially constant parallel to the path of the light beam, wherein the wave plate is disposed between the first optical element and the second optical element.

* * * * *